US00PP12154P2

(12) United States Plant Patent
Heims

(10) Patent No.: US PP12,154 P2
(45) Date of Patent: Oct. 23, 2001

(54) *X HEUCHERELLA* PLANT NAMED 'KIMONO'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/452,028

(22) Filed: Nov. 30, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Klarquist Sparkman Campbell Leigh & Whinston LLP

(57) ABSTRACT

A new and distinct hybrid of *x Heucherella* plant characterized by unique leaf color and shape.

1 Drawing Sheet

The present invention relates to a new and distinct intergeneric hybrid of a Heuchera and a Tiarella, of the family Saxifragaceae, which originated as a cross between an unpatented Heuchera named 'Green Spice' (seed parent) and an unpatented Tiarella named 'Pink Pendant' (pollen parent). Due to the fact that the instant plant and parent plants are the result of crosses between several different Heuchera and/or Tiarella species, no species designations are given.

This new *x Heucherella* is a result of a controlled cross of the aforementioned plants at Terra Nova Nurseries, Inc., in Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant.

This plant is characterized by the following:

1. Unique foliage color.
2. Unique foliage shape.

Asexual propagation by division and tissue culture as done in Canby, Oreg., shows that the foregoing characteristics and distinctions come true to form and are established and transmitted through succeeding propagations.

BRIEF DESCRIPTION OF THE DRAWING

The drawing shows *x Heucherella* 'Kimono' in Canby, Oreg., in July.

DETAILED PLANT DESCRIPTION

The following is a detailed description of the new *x Heucherella* hybrid based on observations of field grown two-year old specimens in Canby, Oreg. The color descriptions are all based on The Royal Horticultural Society Colour Chart.

Foliage:

*Type.*—Simple, semi-evergreen.

*Shape.*—Variable in outline, usually cordate. Palmately lobed. 5–7 lobes. Usually 5 main lobes with primary (central) lobe twice as long as secondary lobes. Primary lobe may split into end lobes that sometimes split again. Usually, the spaces between the primary lobe and secondary lobes are visually significant. Sporadic tendency to narrow to vein width midway along a lobe resulting in an oar-shaped appendage.

*Length.*—5–10 cm.

*Width.*—7–12.5 cm.

*Petiole length.*—13 cm.

*Margins.*—Dentate. Ciliolate.

*Apex (individual lobe).*—Acute to rounded.

*Base.*—Hastate.

*Leaf texture.*—Bristly.

*Petiole texture.*—Villous.

*Leaf arrangement.*—Rosette.

*Venation.*—Reticulate.

Size:

*Height.*—32 cm (2 year old plant grown in Canby, Oreg.).

*Width.*—70 cm (2 year old plant grown in Canby, Oreg.).

Flower:

*Type.*—Perfect, complete.

*Shape.*—Stellate.

*Size.*—7 mm from petal tip to petal tip.

*Petal count.*—5.

*Petal shape.*—Oblanceolate.

*Petal size.*—4 mm. long and to 1 mm wide.

*Calyx shape.*—Campanulate.

*Calyx size.*—4 mm long and to 4 mm wide.

*Sepal count.*—5 parted.

*Sepal shape.*—Oblong where parted.

*Sepal size.*—About 1 mm wide and 4 mm long from sepal tip to pedicel.

*Sepal/calyx texture.*—Pubescent.

*Ovary position.*—Partly inferior.

*Carpel number.*—2.

*Stamen number.*—10.

*Inflorescence type.*—Branched panicle.

*Flower number per inflorescence.*—200–250.

*Peduncle width.*—2–3 mm tapering to 1–1.5 mm.

*Peduncle texture.*—Pubescent.

*Blooming height.*76 cm.

*Bloom period.*—April through July, repeating sporadically in fall in Canby, Oreg.

*Fragrance.*—None.

Fruit:

*Fertility.*—Sterile, no fruit or seed produced.

Habit: Clumping.

Disease: Mild susceptibility to powdery mildew.

Hardiness: Cold hardy to USDA zone 4. Evergreen in USDA zone 6 to 8. Deciduous in zones 4 and 5.

Color characteristics:

*Foliage.*—Spring/Summer: Upper surface. — RHS 137D Green Group. Upper surface, along central vein. — RHS 200C Brown Group. Lower surface. — RHS 138C Green Group. Fall: Upper surface. — RHS 168D Greyed-Orange Group.

*Flower.*—Bud — RHS 160A Greyed-Yellow Group. Petal. — RHS 155D White Group. Sepal. — Lower half is RHS 155D White Group. Upper half is RHS 144B Yellow-Green Group at tip. Anther. — RHS 34A Orange-Red Group. Ovary. — RHS 155B White Group.

*Peduncle.*—RHS 177A Greyed-Orange Group (most prominent near base) side-by-side with RHS 146B Yellow-Green Group.

DESCRIPTION OF PARENT PLANTS

The instant plant resulted from a cross between Heuchera 'Green Spice' and Tiarella 'Pink Pendent'. Both parent plants originated as hybrid crosses at Terra Nova Nurseries, Inc. Both plants are currently commercially available. Heuchera 'Green Spice' was selected as a parent plant for its veiled large leaves with superb color contrast and color lastingness. The instant plant differs from Heuchera 'Green Spice' in having leaves that are uniquely lobed and displays a metallic sheen on its leaf surface. The other parent, Tiarella 'Pink Pendant', was selected for its glossy leaves, branched panicles, and for the dark markings along its main veins. Tiarella 'Pink Pendant' produces oar-shaped appendages sporadically. This characteristic has also been observed in the instant plant. The instant plant differs from Tiarella 'Pink Pendant' in having silver veiling and white flowers.

I claim:

1. A new and distinct hybrid of *x Heucherella* plant substantially as shown and described, characterized by unique leaf color and shape.

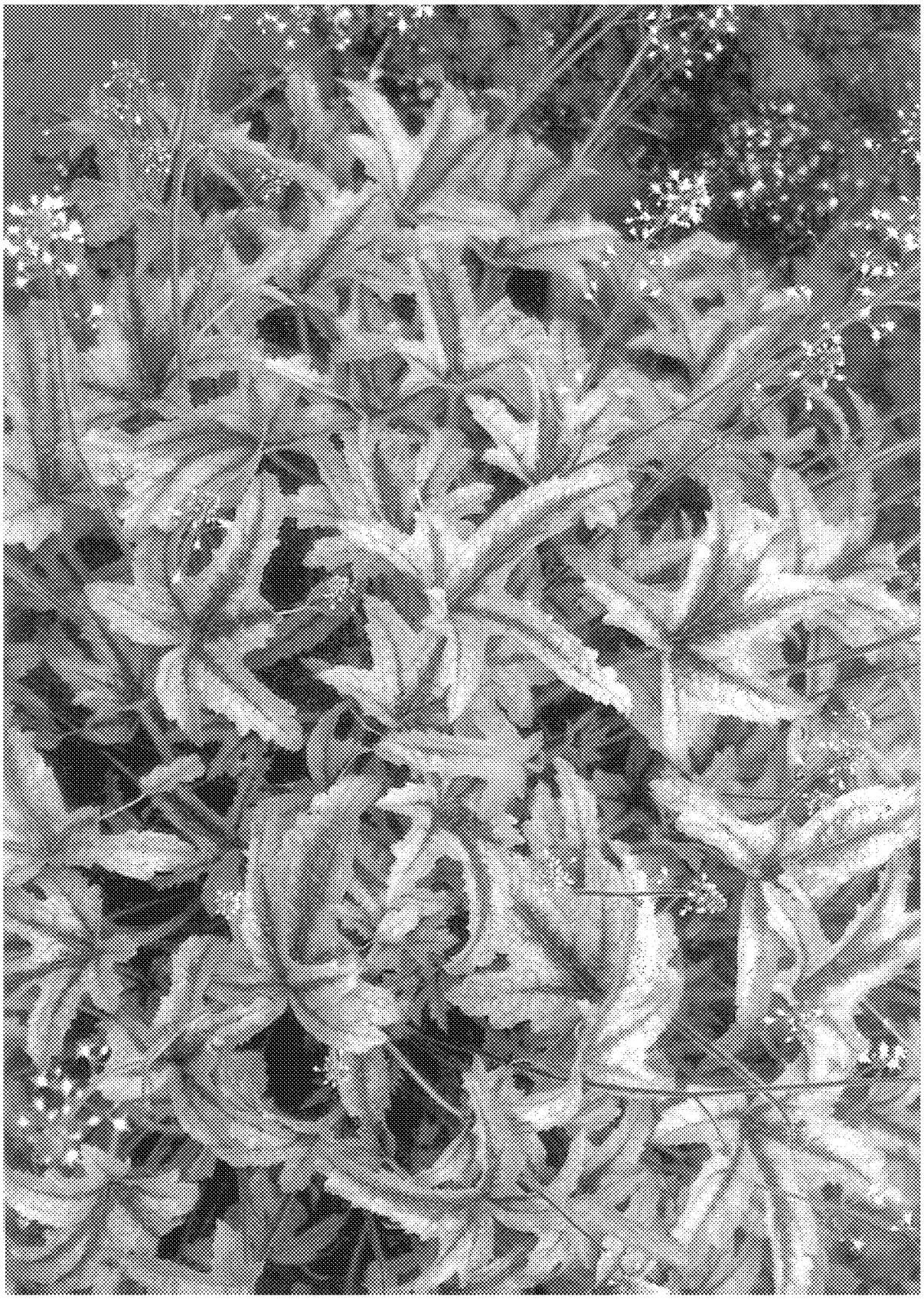

* * * * *